(12) United States Patent
Witte

(10) Patent No.: US 9,910,272 B2
(45) Date of Patent: Mar. 6, 2018

(54) INTEGRATED CAMERA MOUNTING AND IMAGE WINDOW CLEANING DEVICE

(71) Applicant: FORD GLOBAL TECHNOLOGIES, LLC, Dearborn, MI (US)

(72) Inventor: Martin Witte, Warren, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 236 days.

(21) Appl. No.: 14/300,423

(22) Filed: Jun. 10, 2014

(65) Prior Publication Data

US 2015/0353057 A1 Dec. 10, 2015

(51) Int. Cl.
| | |
|---|---|
| *B08B 3/04* | (2006.01) |
| *G02B 27/00* | (2006.01) |
| *H04N 1/00* | (2006.01) |
| *B60S 1/56* | (2006.01) |
| *B60R 11/04* | (2006.01) |
| *B60S 1/08* | (2006.01) |
| *B60S 1/48* | (2006.01) |
| *B60S 1/66* | (2006.01) |
| *G01N 21/15* | (2006.01) |
| *B60R 11/00* | (2006.01) |
| *B60S 1/52* | (2006.01) |

(52) U.S. Cl.
CPC ........... *G02B 27/0006* (2013.01); *B08B 3/04* (2013.01); *B60R 11/04* (2013.01); *B60S 1/0848* (2013.01); *B60S 1/56* (2013.01); *H04N 1/00909* (2013.01); *B60R 2011/004* (2013.01); *B60S 1/48* (2013.01); *B60S 1/52* (2013.01); *B60S 1/66* (2013.01); *G01N 21/15* (2013.01)

(58) Field of Classification Search
CPC ...... B60S 1/52; B60S 1/54; B60S 1/56; B60S 1/485; B60S 1/486; B05B 1/10; B05B 7/0483; B05B 7/0815; B05B 15/0266; B60R 11/04; G01N 21/15; G02B 27/0006; H04N 1/00909; B08B 3/04
USPC ......... 134/18, 113, 198; 239/284.1; 348/148
See application file for complete search history.

(56) References Cited

U.S. PATENT DOCUMENTS

| | | | | |
|---|---|---|---|---|
| 3,059,540 | A | * 10/1962 | Robinson | .............. B60R 1/0602 296/91 |
| 7,138,640 | B1 | * 11/2006 | Delgado | ................ G01N 21/15 250/372 |
| 2002/0005440 | A1 | 1/2002 | Holt et al. | |

(Continued)

FOREIGN PATENT DOCUMENTS

| | | | | |
|---|---|---|---|---|
| CN | 201923085 U | * | 8/2011 | ................ B60S 1/56 |
| CN | 103043035 A | | 4/2013 | |

(Continued)

OTHER PUBLICATIONS

Machine translation of CN 201923085 U, dated Aug. 2011.*

*Primary Examiner* — Michael Wieczorek
*Assistant Examiner* — Kevin G Lee
(74) *Attorney, Agent, or Firm* — Jason Rogers; King & Schickli, PLLC

(57) ABSTRACT

An integrated camera mounting and image window cleaning device includes a mounting bracket, a housing and a seal provided between the housing and the mounting bracket. A delivery channel extends around the outer periphery of the image window of the camera allowing the delivery of cleaning fluid which flows across the entire image window for cleaning.

10 Claims, 7 Drawing Sheets

(56) References Cited

U.S. PATENT DOCUMENTS

| | | | | |
|---|---|---|---|---|
| 2003/0210906 | A1* | 11/2003 | Peterson | G03B 17/02 |
| | | | | 396/427 |
| 2007/0273971 | A1* | 11/2007 | Waldmann | B60R 1/0602 |
| | | | | 359/509 |
| 2009/0250533 | A1 | 10/2009 | Akiyama et al. | |
| 2011/0073142 | A1 | 3/2011 | Hattori et al. | |
| 2011/0292212 | A1* | 12/2011 | Tanabe | B05B 1/08 |
| | | | | 348/148 |
| 2013/0092758 | A1 | 4/2013 | Tanaka et al. | |
| 2013/0146577 | A1 | 6/2013 | Haig et al. | |
| 2013/0319486 | A1 | 12/2013 | Kikuta et al. | |
| 2014/0060582 | A1 | 3/2014 | Hartranft et al. | |
| 2014/0117701 | A1* | 5/2014 | Davis | A42B 3/26 |
| | | | | 296/96.15 |
| 2015/0138357 | A1* | 5/2015 | Romack | G02B 27/0006 |
| | | | | 348/148 |
| 2015/0185592 | A1* | 7/2015 | Eineren | G03B 17/02 |
| | | | | 348/375 |

FOREIGN PATENT DOCUMENTS

| | | | | | |
|---|---|---|---|---|---|
| EP | | 2722234 A1 | * | 4/2014 | B60R 11/04 |
| JP | | 2002240628 A | * | 8/2002 | |
| JP | | 2013006481 A | | 1/2013 | |
| JP | | 2014000949 A | | 1/2014 | |
| WO | WO 2015157744 A1 | | * | 10/2015 | B60S 1/52 |

* cited by examiner

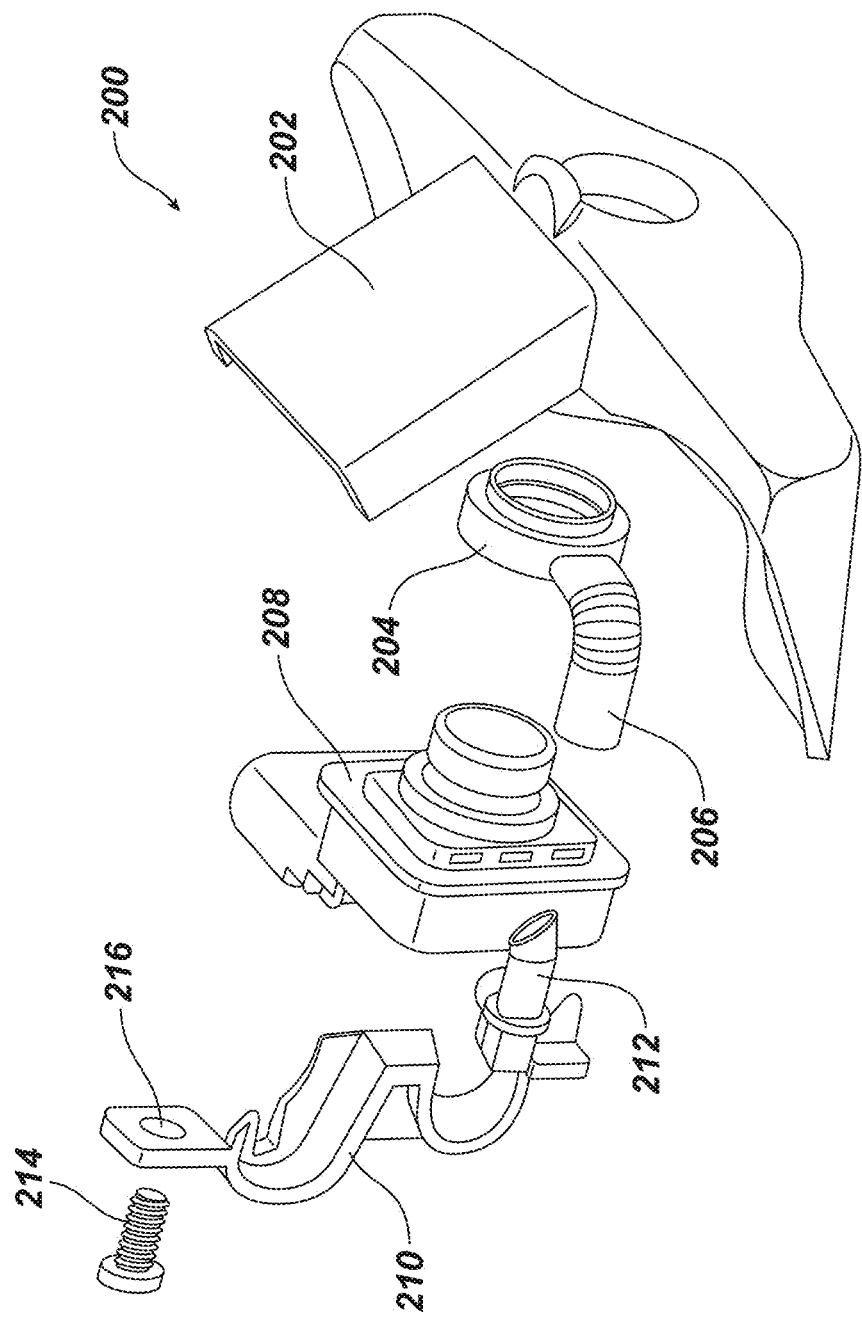

INTEGRATED CAMERA MOUNTING AND IMAGE WINDOW CLEANING DEVICE

TECHNICAL FIELD

This document relates generally to vehicle camera systems and, more particularly, to an integrated camera mounting and image window washing device.

BACKGROUND

The concept of equipping a vehicle with a camera system in order to enhance the visual field of the operator is well known in the art. Such a camera system is particularly useful when backing a vehicle as many vehicles include blind spots that limit the visual field of the driver.

It is also well known in the art to equip cameras, such as rear backup cameras mounted to the bodywork of the vehicle, with washer systems to keep the image window of the camera clear for best visibility. In the past these systems have generally comprised two types. The first includes a gravity flow system wherein the cleaning liquid is delivered through a discharge port above the camera viewing window and then flows as a sheet under the force of gravity across the window to provide cleaning. In an alternative embodiment, the cleaning liquid is delivered to the viewing window through a nozzle with the necessary pressure to discharge the fluid across the image window and provide cleaning.

This document relates to an integrated camera mounting and image window cleaning device that utilizes fewer component parts and requires less assembly time. The device incorporates a water channel in the back side of the bezel in the camera mounting bracket to more efficiently deliver cleaning fluid to the image window. Further the device incorporates a weep system wherein the cleaning fluid is delivered around the full periphery of the viewing window. This ensures that the entire image window is inundated with cleaning fluid so as to provide more effective and efficient cleaning of the image window for enhanced visibility through the camera.

SUMMARY

In accordance with the purposes and benefits described herein, an integrated camera mounting and image window cleaning device comprises a mounting bracket, a housing, a seal provided between the housing and the mounting bracket and a delivery channel extending around an outer periphery of the image window of the camera. Cleaning fluid flows through the delivery channel to wash the image window. In one embodiment the delivery channel is formed in the seal. The seal includes a window opening and the delivery channel extends around that window opening. The mounting bracket and the housing also include window openings.

In one embodiment the device further includes a passageway for delivering cleaning fluid to the delivery channel. That passageway may at least be partially formed by or on the rear face of the housing.

In one embodiment the device further includes a nipple on the mounting bracket. In one embodiment the device includes a cleaning fluid pump and a hose connected between the pump and the nipple. Cleaning fluid is delivered by the pump through the hose and the nipple to the passageway and then to the delivery channel.

In one possible embodiment the seal is a rubber grommet. That grommet includes a lateral extension or lug extending over and closing an open side of the passageway formed by the rear face of the housing. In addition the lug includes an opening through which cleaning fluid is delivered from the nipple on said bracket to the passageway on the housing. Fasteners, such as screws, engage the bracket and the housing and hold the device together.

In one possible embodiment the delivery channel is arcuate and extends through an arc of at least 90 degrees. In another possible embodiment the delivery channel is arcuate and extends through an arc of at least 180 degrees. In yet another possible embodiment the delivery channel is arcuate and extends through an arc of 360 degrees around the image window.

In one possible embodiment an integrated camera mounting and image window cleaning device comprises a mounting bracket for holding the camera, a housing covering the mounting bracket and a weep system for delivering a cleaning fluid through a delivery channel extending around an outer periphery of the image window of the camera. In one embodiment the weep system delivers cleaning fluid through a delivery channel extending around the entire outer periphery of the image window of the camera. Where the image window is round, the delivery channel extends in an arc of 360 degrees around the outer periphery of the image window.

In the following description, there is shown and described several preferred embodiments of the integrated camera mounting and image window cleaning device. As it should be realized, the device is capable of other, different embodiments and its several details are capable of modification in various, obvious aspects all without departing from the system as set forth and described in the following claims. Accordingly, the drawings and descriptions should be regarded as illustrative in nature and not as restrictive.

BRIEF DESCRIPTION OF THE DRAWING

The accompanying drawing incorporated herein and forming a part of the specification, illustrates several aspects of the integrated camera mounting and image window cleaning device and together with the description serves to explain certain principles thereof. In the drawing:

FIG. 6 illustrates a third possible embodiment of the device.

Reference will now be made in detail to the present preferred embodiments of the combined, mounting and image window cleaning device, examples of which are illustrated in the accompanying drawing.

DETAILED DESCRIPTION

Figure 1:
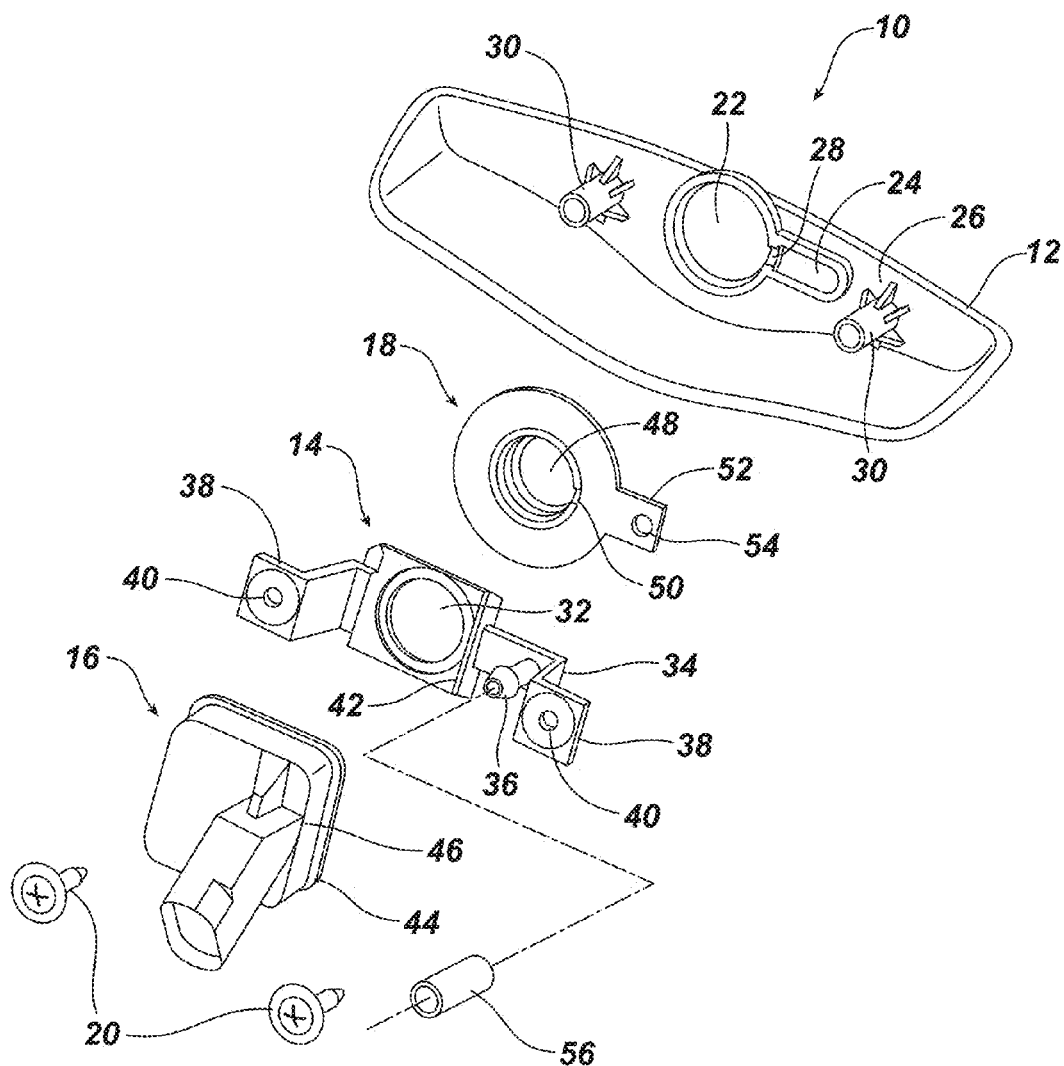
FIG. 1 is an exploded perspective view of the camera mounting and image window cleaning device and a camera.
Figure 2:
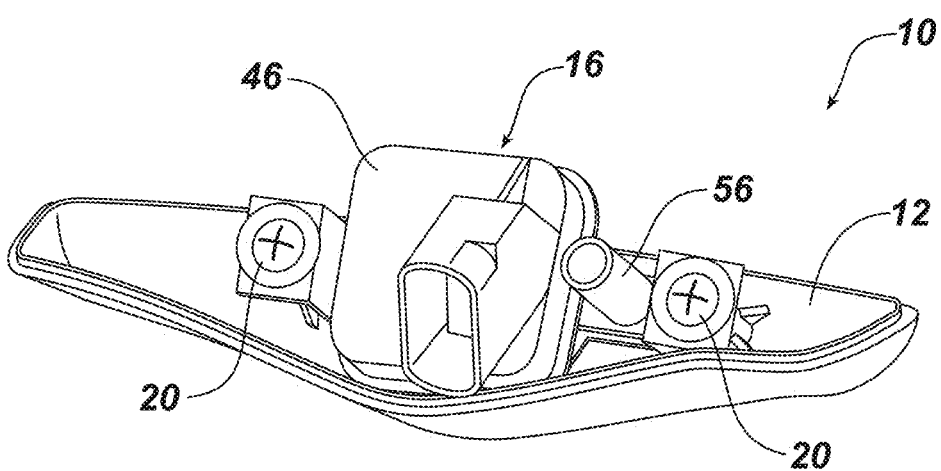
FIG. 2 is a rear perspective view of the device assembled with a camera.
Figure 4:
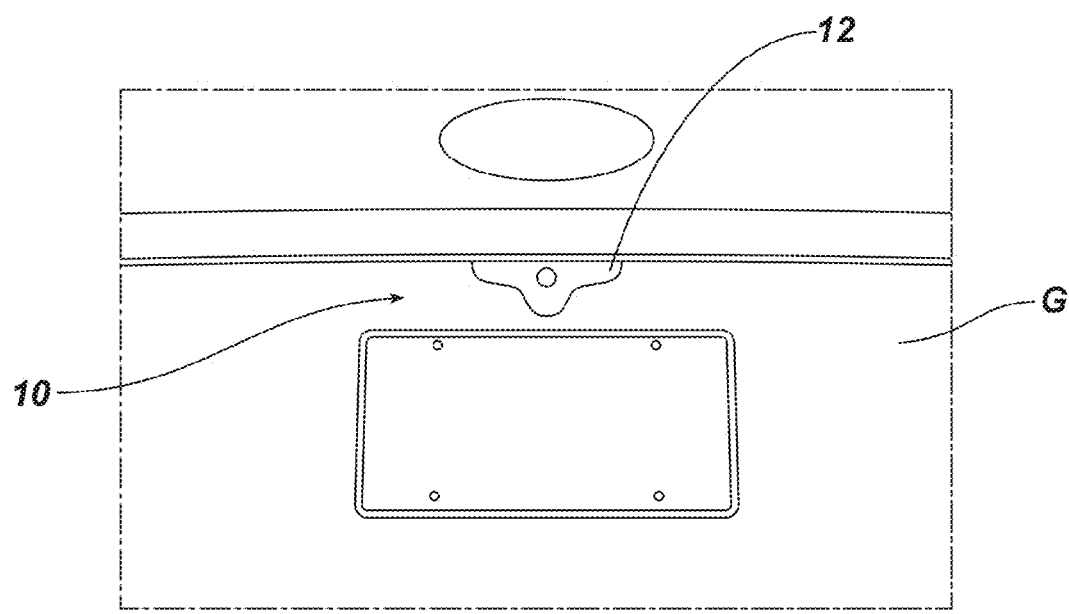
FIG. 4 is a rear view showing the device mounted to the rear of a vehicle.

Reference is now made to FIGS. 1 and 2 illustrating the integrated camera mounting and image window washing device 10. The device 10 includes a housing or aesthetic cover 12, a mounting bracket 14 for holding a camera 16, a cooperating seal 18 and fasteners 20, such as screws, for securing the device together. The housing 12 may be molded from plastic or any other appropriate material. The housing 12 may be formed into substantially any desired aesthetically pleasing shape. Further, the housing 12 may have any desired finish. Thus, for example, the housing 12 may be colored to contrast or match the overall color of the vehicle to which the device 10 is mounted. In another embodiment the housing 12 may, for example, have a chrome finish. The mounting of the device 10 on the tailgate G of an SUV is illustrated in FIG. 4.

As illustrated in FIG. 1, the housing 12 includes a window opening 22. A passageway 24 for delivering cleaning fluid (as described in greater detail below) is formed on a rear face 26 of the housing 12. As illustrated, the passageway 24 includes a port 28 so as to be in open communication with the window 22. As further illustrated in FIG. 1, the housing 12 also includes two bosses 30 for receiving and holding the fasteners 20.

As best illustrated in FIG. 1, the mounting bracket 14, which may be molded from plastic or made from other material is substantially u-shaped. The mounting bracket 14 includes a window opening 32, a laterally projecting lug 34, including a nipple 36, and two opposed mounting flanges 38, each including an opening 40. Tabs 42 on the mounting bracket 14 about the window opening 32 engage the lip 44 on the camera housing 46 to securely hold the camera 16 to the bracket.

Seal 18 includes an image window opening 48. A delivery channel 50 formed in the seal 18 extends around the outer periphery of the image window opening 48. In the illustrated embodiment the image window opening 48 is round and, accordingly the delivery channel 50 is arcuate in shape and extends through an arc of 360 degrees. In other possible embodiments the delivery channel 50 only extends partially around the image window opening 48 such as through an arc of at least 90 degrees or at least 180 degrees. Of course, where the image window opening is square, rectangular or other non-circular shape, the delivery channel may extend around the entire periphery, one half of the periphery, a quarter of the periphery or any other desired amount.

As further illustrated in FIG. 1, the seal 18 includes a lateral extension 52 incorporating an aperture 54. When the mounting bracket 14 is secured to the housing 12 with the fasteners 20, the seal 18 is captured between the bracket and housing. More specifically, the window opening 22 and the housing 12 is aligned with the window opening 48 in the seal 18 and the window opening 32 in the bracket 14. Further, the lateral extension 52 of the seal 18 is aligned with and encloses the open side of the passageway 24 in the housing 12. The nipple 36 is aligned with the aperture 54 in the lateral extension 52 so that the nipple is in communication with the passageway 24 through that aperture. When properly connected, the openings 40 in the mounting flanges 38 of the mounting bracket 14 are aligned with the bosses 30 of the housing 12. The threaded fasteners 20 are inserted through the openings 40 and threadidly engage the bosses 30 so that when tightened, the device 10 is secured together as illustrated in FIG. 2. As should be appreciated, when the camera 16 is properly seated on the mounting bracket 14 as illustrated in FIG. 2, the image window of the camera is aligned with the window openings 22, 32, 48 in the housing 12, bracket 14 and seal 18. For purposes of this document, the image window 62 of the camera 16 is broadly interpreted to include an actual protective image window overlying a camera lens and/or the camera lens itself.

Figure 3:
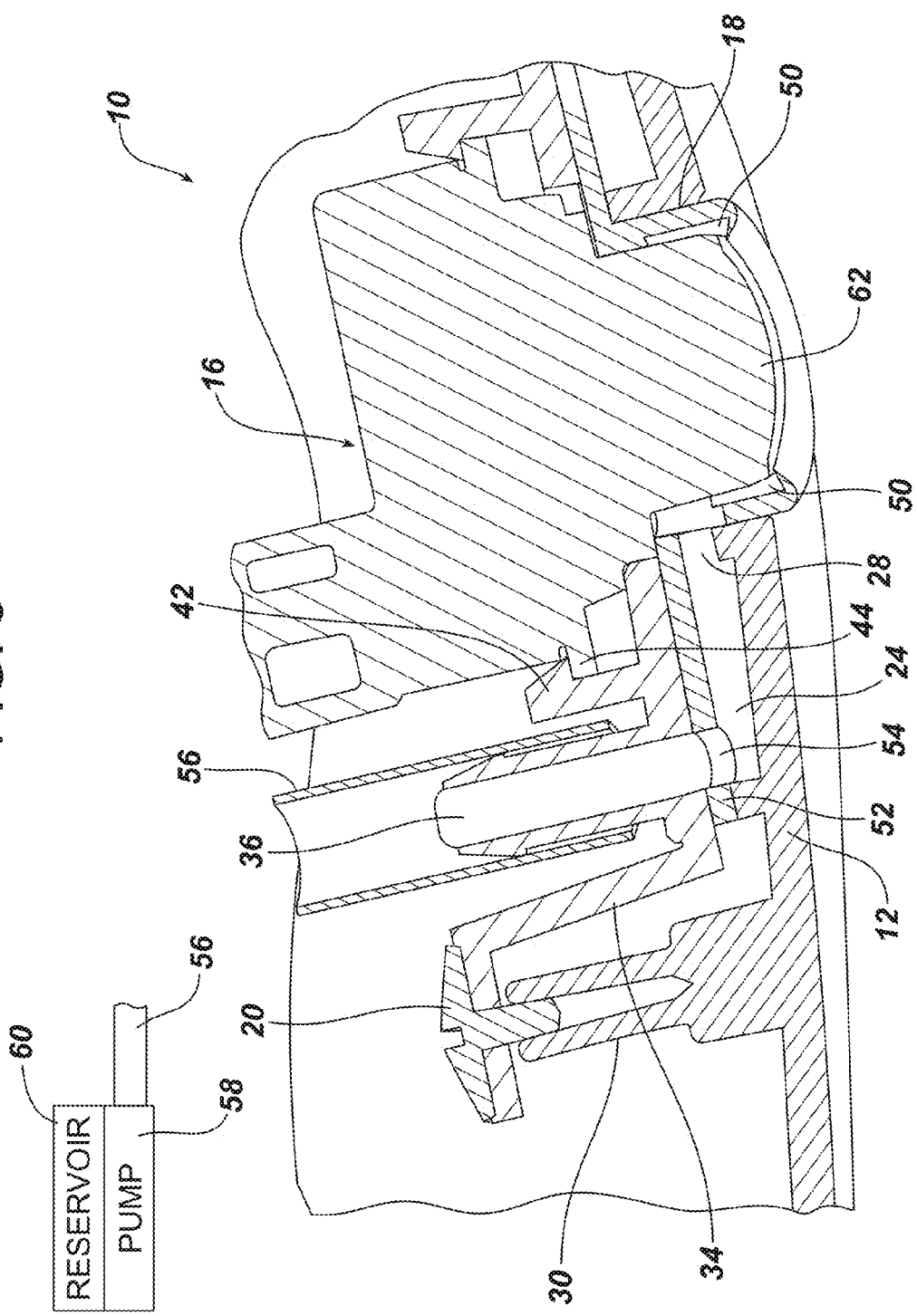
FIG. 3 is a schematical cross-sectional view illustrating the flow path of cleaning fluid from a cleaning fluid reservoir to the image window of the camera being cleaned with the cleaning fluid.

As best illustrated in FIG. 3, a hose 56 is secured to the nipple 36. The hose 56 is connected to a pump 58 which pumps cleaning fluid such as windshield washer fluid or other appropriate fluid from a reservoir 60. When it is desired to wash or clean the image window 62 of the camera 16, the pump 58 is energized. Washer fluid from the reservoir 60 is then serially moved by the pump 58 through the hose 56, the nipple 36, the aperture 54 in the seal 18, and then through the passageway 24 formed in the housing 12 through the port 28 to the delivery channel 50. In the illustrated embodiment, the delivery channel 50 extends in an arc of 360 degrees completely around the image window 62 of the camera 16 thereby forming a weep system for delivering cleaning fluid around the entire outer periphery of the camera image window. This allows for total cleaning of the image window 62 in a more effective and efficient manner. The weep delivery of cleaning fluid around the entire 360° periphery of the image window 62 ensures full and complete cleaning of the window under substantially any conditions.

Figure 5A:
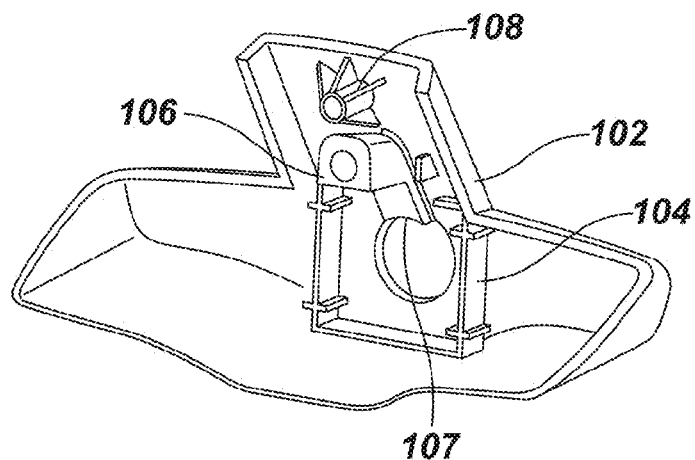
FIGS. 5*a*-5*d* are a series of perspective views illustrating a second embodiment of the device.

FIGS. 5a-5d illustrate a second embodiment of an integrated camera mounting and image window cleaning device 100. FIG. 5a illustrates the rear of the housing 102 including a camera support 104, cleaning fluid delivery element 106 and mounting screw boss 108. The delivery element 106 provides cleaning fluid around an arc 107 provided adjacent the top of the image window 109 of the camera 110.

Figure 5B:
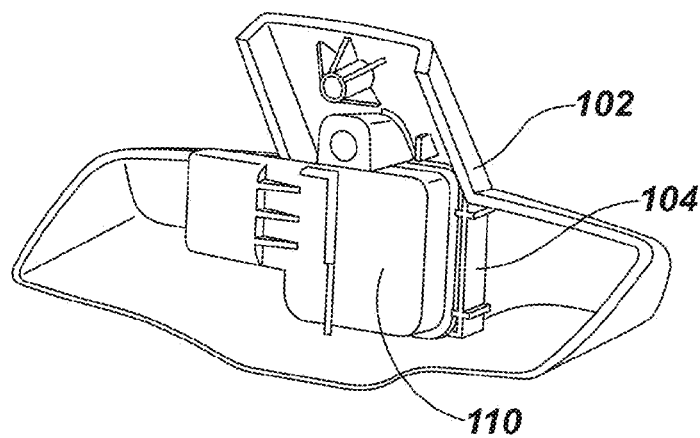
Figure 5C:
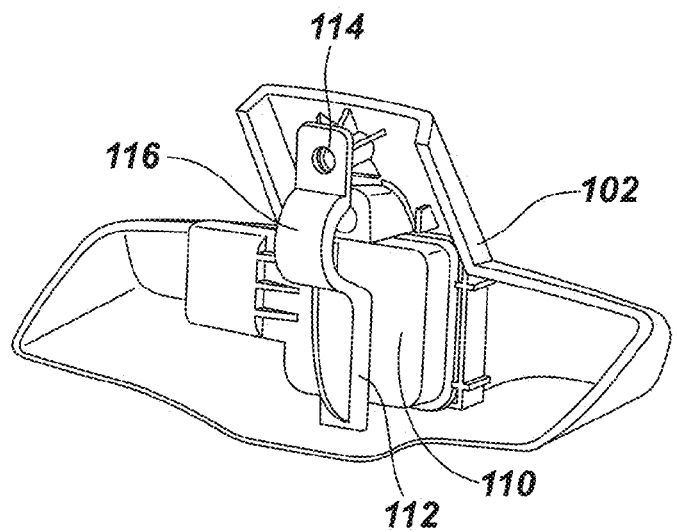
Figure 5D:
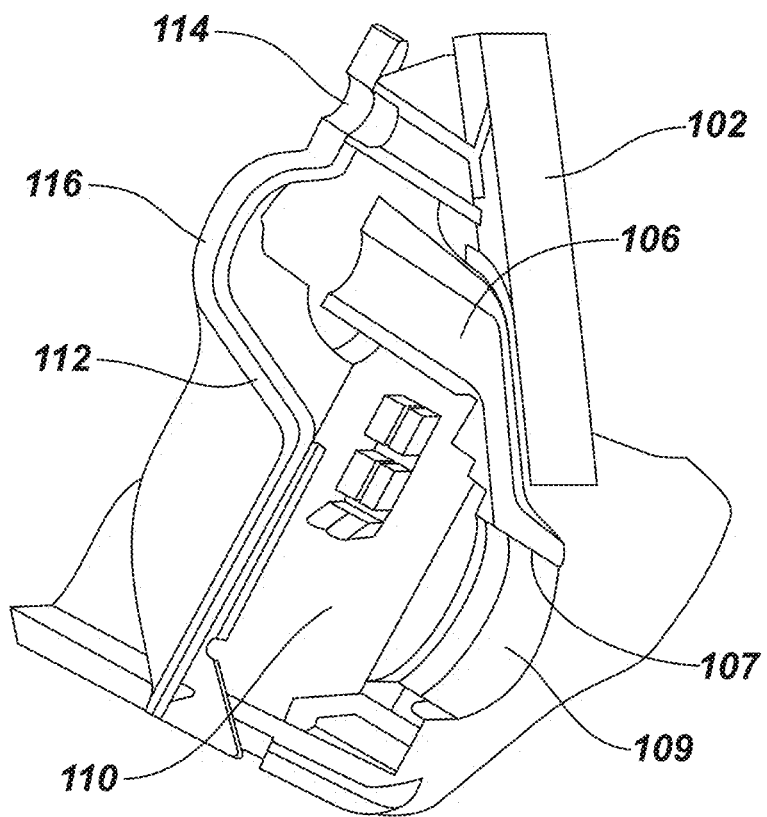

FIG. 5b illustrates the camera 110 received in the support 104. FIG. 5c shows the mounting bracket 112 received over the camera 110. The bracket 112 includes an aperture 114 aligned with the screw boss 108 that receives a fastening screw (not shown) which secures the assembly together. The bend 116 in the bracket provides an opening allowing a cleaning fluid delivery hose (not shown) to be connected to the element 106. FIG. 5d shows the complete assembly 100 in cross section.

FIG. 6 illustrates yet another embodiment of the device 200 including a housing 202, seal 204 with 360° weep channel (not visible in figure) and integral fluid delivery hose 206, camera 208, mounting bracket 210, hose connector 212 and fastening screw 214 which passes through hole 216 in bracket and is secured in screw boss (not visible) on back of housing.

In summary, numerous benefits are provided by the integrated mounting and image window cleaning device 10. By integrating camera mounting and image window cleaning into a single device through the incorporation of cleaning fluid delivery passageways in the mounting bracket (note nozzle 36), housing 12 (note passageway 24) and seal 18 (note aperture 54, lateral extension 52 closing passageway 24 and delivery channel 50), a less complicated assembly is provided with fewer parts which is easier and less expensive to manufacture. Further, by providing the delivery of cleaning fluid by means of a weep system around the entire periphery of the image window 62 of the camera 16, the most effective and efficient cleaning of that window is possible.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. An integrated combined camera mounting and image window cleaning device for cleaning an image window of a camera, comprising:

a mounting bracket;

a housing having a window opening;

a seal provided between said housing and said mounting bracket, wherein said seal is a rubber grommet having an image window opening;

a delivery channel formed in the seal and extending around an outer periphery of the image window opening of the seal and around an outer periphery of the image window of said camera and through which cleaning fluid flows to wash said image window; and a passageway formed on a rear face of the housing, wherein the passageway is in fluid communication with the delivery channel for delivering cleaning fluid to the delivery channel.

2. The device of claim 1, wherein said mounting bracket and said housing also include window openings.

3. The device of claim 2, further including a nipple on said mounting bracket.

4. The device of claim 3, further including a cleaning fluid pump and a hose connected between said pump and said nipple, cleaning fluid being delivered by said pump through said hose and said nipple to said passageway and then to said delivery channel.

5. The device of claim 4, wherein said grommet includes a lateral extension extending over and closing an open side of said passageway.

6. The device of claim 5, wherein said lateral extension includes an opening through which cleaning fluid is delivered from said nipple on said mounting bracket to said passageway on said housing.

7. The device of claim 1, further including fasteners for engaging said mounting bracket and said housing and holding said device together.

8. The device of claim 1, wherein said delivery channel is arcuate and extends through an arc of at least 90 degrees.

9. The device of claim 1, wherein said delivery channel is arcuate and extends through an arc of at least 180 degrees.

10. The device of claim 1, wherein said delivery channel is arcuate and extends through an arc of 360 degrees around said window.

* * * * *